(12) United States Patent
Kawata

(10) Patent No.: US 6,254,464 B1
(45) Date of Patent: Jul. 3, 2001

(54) HAND SCALER POLISHING UNIT AND HAND SCALER POLISHING APPARATUS

(75) Inventor: Sosaku Kawata, Kanuma (JP)

(73) Assignee: Nakanishi Inc., Tochigi (JP)

( * ) Notice: Subject to any disclaimer, the term of this patent is extended or adjusted under 35 U.S.C. 154(b) by 0 days.

(21) Appl. No.: 09/581,844

(22) PCT Filed: Oct. 21, 1998

(86) PCT No.: PCT/JP98/04762

§ 371 Date: Jun. 19, 2000

§ 102(e) Date: Jun. 19, 2000

(87) PCT Pub. No.: WO00/23227

PCT Pub. Date: Apr. 27, 2000

(51) Int. Cl.[7] .................................................. B24B 7/00
(52) U.S. Cl. ........................ 451/164; 451/162; 451/168; 451/356
(58) Field of Search .................................. 451/162, 163, 451/164, 168, 356

(56) References Cited

U.S. PATENT DOCUMENTS

| 2,578,081 | * | 12/1951 | Miller et al. | 451/164 |
| 2,703,470 | * | 3/1955 | Porter et al. | 451/164 |
| 3,133,381 | * | 5/1964 | Freed | 451/164 |
| 3,576,089 | * | 4/1971 | Magnuson | 451/356 |
| 4,179,850 | * | 12/1979 | Gillette | 451/164 |
| 5,155,939 | * | 10/1992 | Pheulpin | 451/162 |
| 5,643,059 | * | 7/1997 | Chen | 451/356 |
| 5,667,434 | * | 9/1997 | Prusaitis et al. | 451/552 |

FOREIGN PATENT DOCUMENTS

| 5-29661 | 7/1987 | (JP) . |
| 1-146650 | 6/1989 | (JP) . |
| 5-503667 | 6/1993 | (JP) . |
| 9-511951 | 10/1995 | (JP) . |

* cited by examiner

Primary Examiner—Eileen P. Morgan
(74) Attorney, Agent, or Firm—Keil & Weinkauf

(57) ABSTRACT

A hand scaler sharpener unit adapted to sharpen a hand scaler with a grindstone for restoration of the hand scaler, including a base member having a base surface slanted at an angle to a level line, a grindstone mounting member for mounting a grindstone thereon, a grindstone driving means for reciprocatingly moving the grindstone mounting member along the base surface, as well as a hand scaler sharpening apparatus including this hand scaler sharpener unit and a hand scaler securing unit for securing a hand scaler generally vertically during operation of the sharpener unit.

7 Claims, 10 Drawing Sheets

HAND SCALER POLISHING UNIT AND HAND SCALER POLISHING APPARATUS

FIELD OF ART

The present invention relates to a hand scaler sharpener unit and a hand scaler sharpening apparatus. In particular, the invention relates to a hand scaler sharpener unit for restoring mainly the cutting edge of a hand scaler by sharpening the same with a grindstone, which hand scaler is commonly used in periodontal treatment for manual removal of dental calculus, dental plaque, or necrotized cementum, or for manual polishing of root surfaces, as well as to a hand scaler sharpening apparatus having this hand scaler sharpener unit and a hand scaler securing unit for securing a hand scaler.

BACKGROUND ART

A hand scaler is widely used as a hand tool for removing dental calculus and the like. A hand scaler as shown in FIG. 14 and designated as 1, may be segmented into a grip section 2 which is grasped by an operator, shank sections 3 which are contiguously provided usually at the ends of the grip section 2 and bent as required, and blade sections 4 each of which is provided at the tip of each shank section 3. One of the blade sections 4, which are double-edged, is shown enlarged and in section in FIGS. 15 and 16, respectively. The blade section 4 has an inner face 4*a*, right and left sides 4*b*, and a curved back face 4*c*. The inner face 4*a* and each of the right and left sides 4*b* form a sharp edge, which substantially functions as a cutting edge 5 for removing dental calculus or for performing other treatments.

When the cutting edge 5 becomes dull as a result of use, the edge 5 can hardly catch calculus, resulting in decreased treatment efficiency. In addition, the operator is likely to exert excess force to the scaler 1 to cause wound in the gum or periodontal tissues of a patient or to cause damage to the scaler 1. For obviating such danger, the cutting edge 5 has to be restored by proper sharpening with a grindstone.

Conventional methods for restoring the cutting edge may be divided into manual sharpening wherein a surface of a grindstone in the form of a rectangular plate is placed to the side 4*b* of the scaler blade section 4, and moved up and down along the side 4*b* with a hand, and motor-assisted sharpening wherein a grindstone in the form of a circular disk is rotated by a motor, and the side 4*b* of the blade section is held to the peripheral surface of the grindstone.

The manual restoration of the cutting edge is carried out with the scaler 1 in one hand and the grindstone in the other hand, adjusting the angle of the grindstone surface to the inner face 4*a* in conformity with the angle of the cutting edge 5. It is thus much more laborious than the motor-assisted sharpening, and is particularly difficult for an inexperienced beginner. Even the angles adjusted by skilled operators may have individual difference, and the finishing may not be uniform.

Restoration of the cutting edge by the motor-assisted sharpening also has problems. For example, the side 4*b* of the blade section is sharpened with the curved outer peripheral surface of a grindstone, so that restoration of the cutting edge to exactly the original angle before wearing is hard to achieve, compared to the manual sharpening using a flat grindstone surface. This, in combination with continuous rotation of the grindstone, often leads to excess grinding of the scaler.

DISCLOSURE OF THE INVENTION

It is an object of the present invention to provide a hand scaler sharpener unit that is capable of easily restoring the cutting edge of a hand scaler to its original angle.

It is another object of the present invention to provide a hand scaler sharpening apparatus that enables even a beginner to restore the cutting edge of a hand scaler easily and uniformly.

According to the present invention, there is provided a hand scaler sharpener unit adapted to sharpen a hand scaler with a grindstone for restoration of the hand scaler, comprising:

a base member having a base surface slanted at an angle to a level line, a grindstone mounting member for mounting a grindstone thereon, and a grindstone driving means for reciprocatingly moving said grindstone mounting member along said base surface.

According to the present invention, there is also provided a hand scaler sharpening apparatus comprising the hand scaler sharpener unit mentioned above, and a hand scaler securing unit for securing a hand scaler generally vertically during operation of the sharpener unit.

PREFERRED EMBODIMENT OF THE INVENTION

Figure 1:
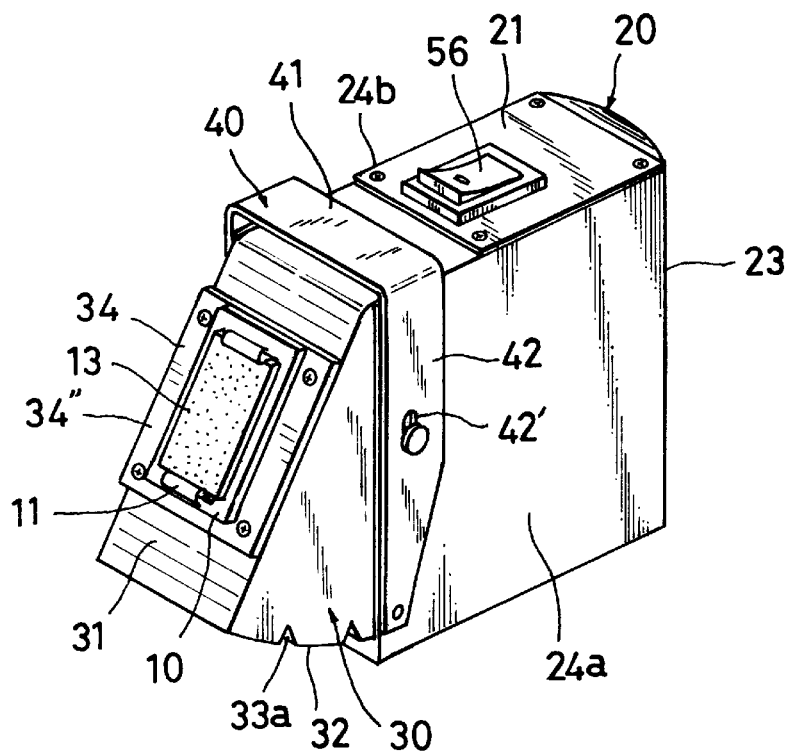
FIG. 1 is a perspective view of an embodiment of a hand scaler sharpener unit according to the present invention.

The hand scaler sharpener unit of the present invention essentially has a base member having a base surface slanted at an angle to the level line, a grindstone mounting member for mounting a grindstone thereon, and a grindstone driving means for driving the grindstone via the grindstone mounting member. The grindstone may be a commercially available grindstone in the form of a plate, and in particular a grindstone in the form of a rectangular plate is preferably used. The slant angle of the base surface defined on the base member may be designed variably as will be discussed later. When the base surface is fixedly designed at a predetermined slant angle, the angle is preferably set at 60 to 80 degree so as to correspond to the most common angle of the scaler cutting edge.

The grindstone mounting member is attached with respect to the base member with the grindstone mounting member being placed on the base surface, and reciprocatingly moved up and down (up and down along the slant of the base surface) on the base surface by the grindstone driving means. This reciprocating motion enables the grindstone mounted on the grindstone mounting member to simulate automatically and accurately the motion (up and down motion) of a grindstone that is manually imparted during manual restoration of the cutting edge. By contacting the side of the scaler blade section in parallel to the surface of the grindstone driven in this manner, the cutting edge of the scaler can be restored easily to its original angle before wearing.

According to the present invention, the base member may be composed of separate parts, namely a stationary body and a movable body provided with the base surface, and the movable body may be rotatably connected to the stationary body by means of a suitable shaft member or the like means. The base member may further be provided with a slant angle setting means for securing the movable body with respect to the stationary body at an appropriate rotational angular position, so that the base member is designed to have capacity to vary the slant angle of the base surface as desired. Thus the sharpener unit of the present invention is easily adapted to a variety of hand scalers with varying cutting edge angles. The slant angle setting means may be, in a simplest form, a stopper using a pin, a screw, or the like, that is capable of securing the movable body with respect to the stationary body at an appropriate rotational angular position. With such a structure, the slant angle of the base surface may be changed steplessly. In the present invention, however, the slant angle setting means is structured as follows so as to facilitate and accelerate adjustment of the slant angle of the base surface.

According to the present invention, the movable body may be provided with a curved surface that curves in the direction of rotation of the movable body, and the slant angle setting means may be composed of a first elastic member for continuously thrusting the movable body in one direction of rotation, a plurality of recesses provided on the curved surface at predetermined intervals in the direction of rotation, an engagement member provided on the side of the stationary body for engaging with a desired one of the recesses, a second elastic member for continuously thrusting the engagement member toward engagement with the one of the recesses, and an operation member for releasing the engagement of the engagement member with the one of the recesses against the thrust of the second elastic member. In this structure, the engagement member on the side of the stationary body is thrust by the second elastic member toward engagement with one of the recesses on the side of the movable body, which engagement between the engagement member and the recess secures, with respect to the stationary body, the movable body that is thrust to rotate in one direction by the first elastic member. In this state, the base surface of the movable body is set at a slant angle corresponding to the selected one of the recesses. The slant angle of the base surface may be changed by operating the operation member to detach the engagement member from the recess against the thrusting force of the second elastic member, thereby releasing the movable body from the stationary body. After the release, the movable body that is thrust to rotate in one direction by the first elastic member is moved manually in one direction of rotation or the other as desired, to place another one of the recesses in the position corresponding to the direction of engagement of the engagement member. When the operational member is released in this state, the engagement member is displaced again toward engagement by the action of the second elastic member to engage with the above-mentioned another one of the recesses. This engagement re-secures the movable body with respect to the stationary body at a rotational angular position that is different from the first one, with the base surface set at a slant angle corresponding to the above-mentioned another one of the recesses. Thus, the change of the slant angle of the base surface may be achieved by simple operations including operation of the operation member, adjustment of the rotational angular position of the movable body, and release of the operation member. Further, in these operations, since the positional adjustment of the movable body is effected by placing, facing to the engagement member, a selected one of the plurality of recesses that have been provided on the curved surface of the movable body for indexing a plurality of preferable slant angles of the base surface, the slant angle may be set more promptly and accurately without the need for an angle index, compared to the stepless change of the slant angle of the base surface.

The recesses may preferably be in the form of, for example, grooves or apertures. The engagement member may be in the form of, for example a rod member engageable with one of the grooves or a pin insertable into one of the apertures, as long as the engagement member is capable of detachably fitted in one of the recesses.

The first elastic member may preferably be a torsion coil spring that is mounted around a shaft member or a shaft portion for rotatably connecting the movable body with respect to the stationary body. The second elastic member may preferably be a coil spring.

In the present invention, the curved surface is provided with the recesses at 10° intervals in the direction of rotation, so that the slant angle of the base surface may be varied in steps of 10°. Preferred slant angles of the base surface established by the recesses are, for example, 40°, 50°, 60°, 70°, 80° and 90°. This setting enables application of the sharpener unit of the present invention not only to standard scalers, but also to scalers having their cutting edges deformed due to manual sharpening.

In the hand scaler sharpener unit of the present invention, the grindstone driving means may be composed of a motor, an eccentric shaft driven by the motor to make a circular motion, and a driving direction converting means for converting the circular motion of the eccentric shaft to an up-and-down reciprocating motion of the grindstone mounting member along the base surface.

The driving direction converting means may, in turn, be composed of a direction converting member having a horizontally extending slot for receiving the eccentric shaft therein, and a guide member for guiding the displacement of the direction converting member only in the up-and-down direction. With this structure, the circular motion of the eccentric shaft driven by the motor displaces the direction converting member which receives the eccentric shaft in its slot, but such displacement of the direction converting member is restricted to only up-and-down direction by means of the guide member. As a result, the direction converting member is reciprocatingly moved up and down within a range corresponding to the component of the up-and-down displacement of the circular motion of the eccentric shaft, and such reciprocating motion is transferred to the grindstone mounting member. The slot may have any length as long as it covers the diameter of the circular motion of the eccentric shaft.

According further to the present invention, the direction converting member may be connected to the grindstone mounting member, or the grindstone mounting member may be made to function also as a direction converting member. In the latter embodiment, the above-mentioned slot is to be provided on the rear surface of the grindstone mounting member.

The hand scaler sharpening apparatus of the present invention is composed of the hand scaler sharpener unit as mentioned above, and a hand scaler securing unit for fixing a hand scaler generally vertically during operation of the sharpener unit. According to the present invention, a scaler is secured in a predetermined position by means of the securing unit during operation of the sharpener unit, allowing easy and uniform restoration of the original cutting edge of a hand scaler even by a beginner.

According to the present invention, the hand scaler securing unit may be composed of a securing unit body and a support member for supporting the securing unit body in a predetermined upper position. According further to the present invention, the securing unit body may be composed of a stationary member fixed to the support member, a scaler clamping member for clamping a scaler grip section between the stationary member and the scaler clamping member, a distance adjusting means for adjusting the distance of the scaler clamping member from the stationary member, and a securing means capable of securing the scaler clamping member with the scaler grip portion being clamped between the stationary member and the clamping member. The securing means is designed to be capable of securing the scaler clamping member by constraining the distance adjusting means, and to gradually increase the constraining force exerted on the distance adjusting means as the scaler clamping member moves closer to the stationary member.

Specific examples of the scaler clamping member include an annular roller (a cam roller). Specific examples of the distance adjusting means include an eccentric cam having a cam body in the form of a circular disk around which the roller is rotatably (not integrally) fitted, and a cam shaft extending eccentrically from the cam body. This structure allows the roller to move away or closer with respect to the stationary member by varying the diameter of the cam (diameter of the cam body with respect to the cam shaft center) facing to the stationary member by means of rotation of the cam shaft.

Specific examples of the securing means include a structure wherein an external thread is provided on the cam shaft and an internal thread is provided on an axial bore through a cam shaft support member that receives and supports the cam shaft in the axial bore, so that when the cam shaft is rotated in a direction to cause the roller to move closer to the stationary member, the tightening force between the external and internal threads gradually increases, whereas when the cam shaft is rotated in the opposite direction, the tightening force between the external and internal threads gradually decreases. The increasing tightening force between the external and internal threads gradually constrains the cam shaft and the cam body, which causes securing of the roller with the scaler grip section being clamped between the stationary member and the roller.

EXAMPLES

Preferred embodiments of the present invention will now be explained with reference to the attached drawings.

Figure 2:
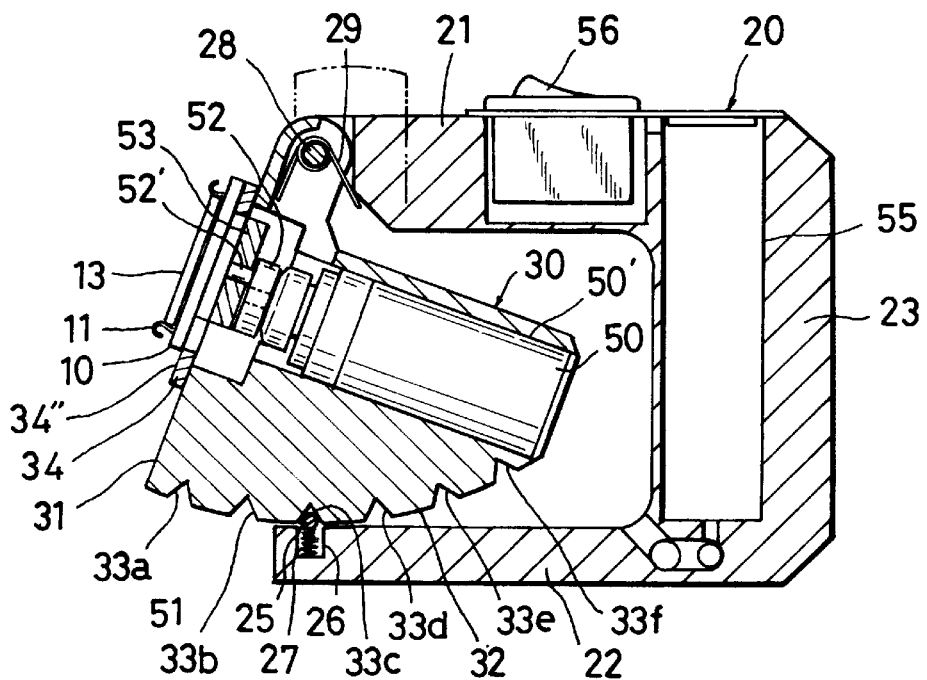
FIG. 2 is an explanatory view of the hand scaler sharpener unit of FIG. 1, seen radioscopically from the side.
Figure 3:
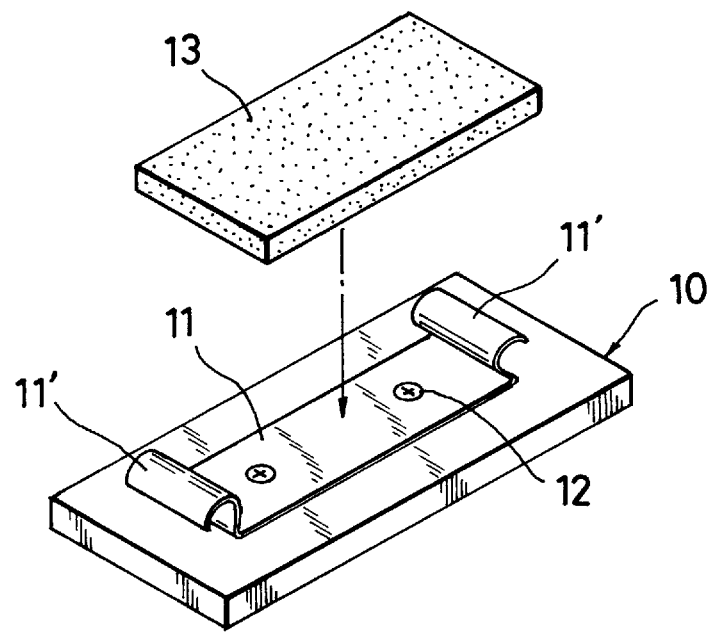
FIG. 3 is a perspective view showing a grindstone and a grindstone mounting member for mounting the grindstone.

The hand scaler sharpener unit as shown in FIGS. 1 and 2 is composed of a grindstone mounting member 10 in the form of a rectangular plate for mounting thereon the grindstone 13 shaped into a rectangular plate, and a base member onto which the grindstone mounting member 10 is attached. The base member has a stationary body 20 in the form of a hollow case opened to the front, and a movable body 30 that is accommodated in the stationary body 20 and may be drawn out through the opening. On the upper surface of the grindstone mounting member 10 is fixed a grindstone holder 11 formed of a thin metal plate with flat countersunk head screws 12, as shown in FIG. 3. The grindstone holder 11 has plate spring portions 11' which have been formed by curving the longitudinal ends of the thin plate so as to give plate spring-like elasticity. The grindstone 13 may be attached to and detached from between the plate spring portions 11' by a one-touch operation.

The stationary body 20 has an upper part 21, a lower part 22, a rear part 23, and right and left side plates 24a, 24b, which together define an internal space therein. The movable body 30 is rotatably connected to the stationary body 10 via a rotation shaft 28 (FIG. 2) provided transversely between the right and left side plates 24a and 24b of the stationary body 10 in the upper front position thereof. Around the rotation shaft 28 is fitted a torsion coil spring 29 as a first elastic member for continuously thrusting the movable body 30 rotationally forward (toward the projecting direction).

The movable body 30 has a front surface 31, which is always exposed through the opening of the stationary body 20, and onto which a guide member 34 to be discussed later is screwed. The surface of the guide member 34 defines a base surface 34" onto which the grindstone mounting member 10 is placed.

Figure 4:
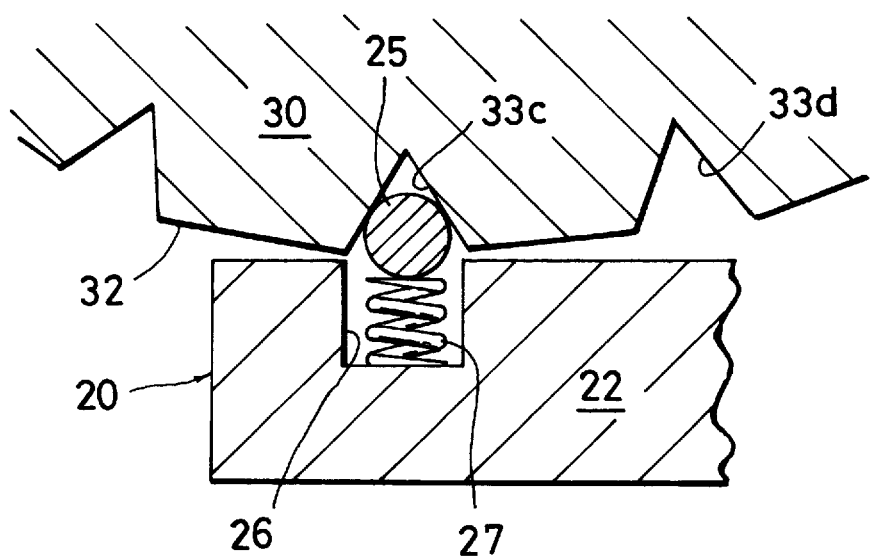
FIG. 4 is a partially enlarged cross-sectional view of the rod member and an indexing groove in the engaged state.
Figure 5:
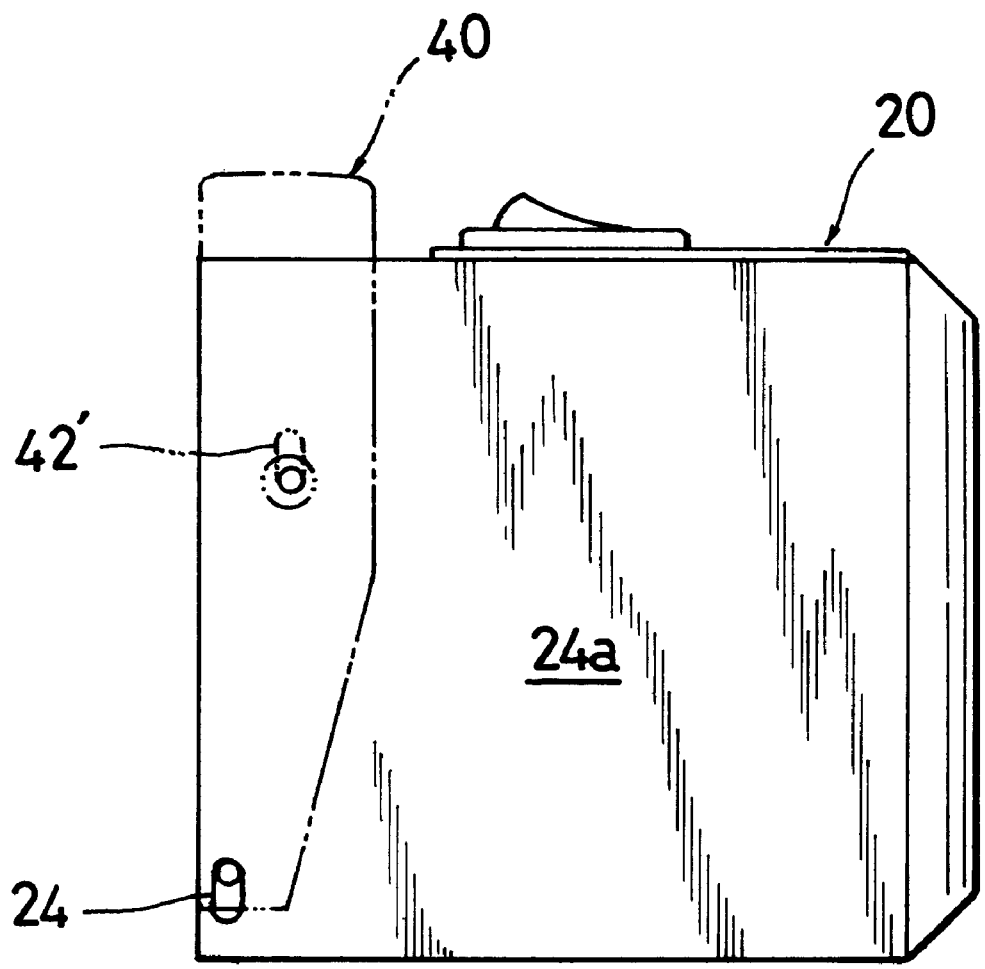
FIG. 5 is a right side view of a stationary body with an operation member being shown radioscopically.

The movable body 30 further has a lower surface 32 curved along the direction of rotation around the rotation shaft 28. The lower surface 32 is provided with transversely extending first to sixth indexing grooves 33a, 33b, 33c, 33d, 33e, 33f as recesses at 10° intervals in the direction of rotation. The lower part 22 of the stationary body 20 is also provided with a transversely extending groove 26 in its upper surface at a location where the lower surface 32 of the movable body 30 gets closest to the upper surface. The groove 26 accommodates therein a rod member 25 as an engagement member as shown in FIG. 4, which member 25 is continuously thrust in the direction to get out of the groove 26 (upward) by means of coil springs 27 as second elastic members arranged at both ends of the groove 26. When any one of the indexing grooves on the movable body 30 is placed right above the groove 26, the rod member 25 gets out of the groove 26 due to the thrusting force applied by the springs 27 to enter the indexing groove that faces to the groove 26. The ends of the rod member 25 slightly project out of the stationary body 20 through slots 24' (FIG. 5) that are relatively long in the vertical direction and provided through the right and left side plates 24a, 24b in a lower front position thereof, and connect to an operation member 40. Since the rod member 25 is disposed on the side of the stationary body 20 via the slots 24', the movable body 30 that is thrust by the torsion coil spring 29 to project through the opening of the stationary body 20 is secured with respect to the stationary body 20 with the rod member 25 entered one of the indexing grooves.

The operation member 40 is composed of right and left side frames 42, to the lower end of which the ends of the rod member 25 are connected, and an operation knob 41 connecting the upper ends of the right and left side frames 42. Each of the right and left side frames 42 has a slot 42' in the middle portion, which slot is relatively long in the vertical direction. The right and left side frames 42 are attached to the right and left side plates 24a, 24b of the stationary body 20 with pins via the slots 42' with allowance of vertical displacement for the length of the slots 42'.

The movable body 30 has a motor cavity 50' for accommodating a motor 50 therein with the output axis (not shown) of the motor 50 extending perpendicular to and to the close proximity of the front surface 31 of the movable body 30. A battery (two AA cells) as a power supply for the motor 50 is accommodated in a battery boxy 55 provided in the rear part 23 of the stationary body 20, and a switch 56 for the motor 50 is disposed in the upper part 21 of the stationary body 20.

Figure 6:
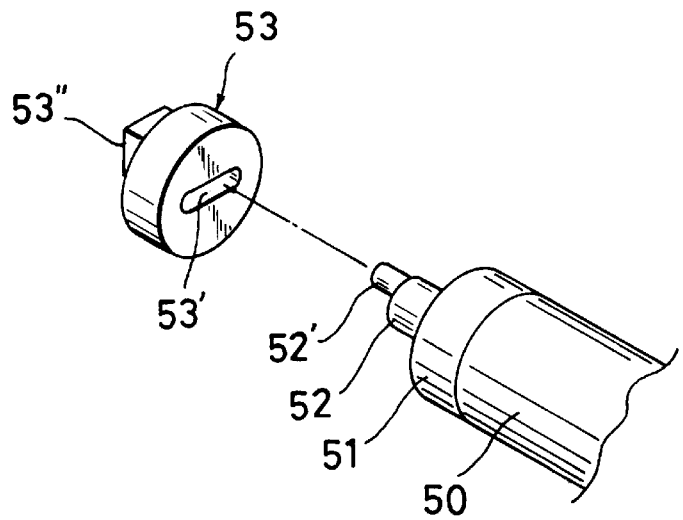
FIG. 6 is an exploded perspective view of an eccentric shaft and a direction converting member in a detached state.
Figure 7:
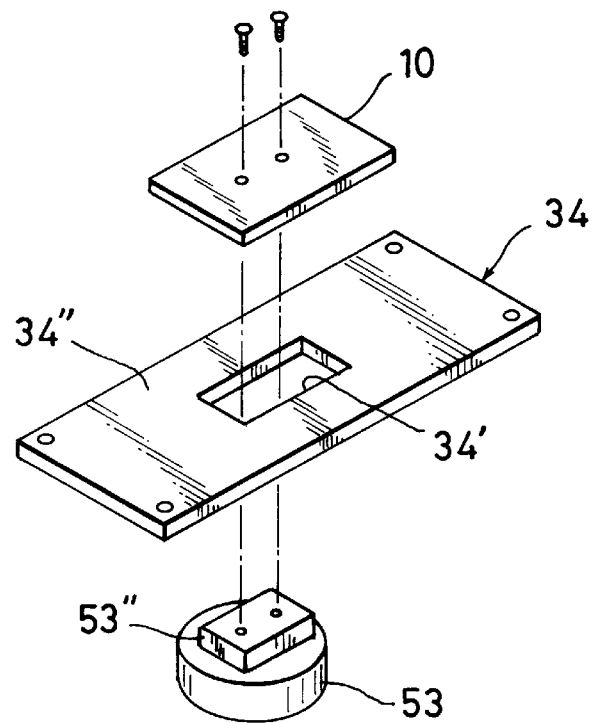
FIG. 7 is an exploded perspective view of a grindstone mounting member, a guide member, and the direction converting member in a detached state.

As shown in FIG. 6, a rotary member 52 having an eccentric shaft 52' is connected to the output axis of the motor 50 via conventional reduction gears 51 having a sun-planetary gear structure. The rotary member 52 is connected to a direction converting member 53 so that the eccentric shaft 52' is received in a horizontally extending slot 53' provided on the rear surface of the direction converting member 53. On the front surface of the direction converting member 53 is provided a vertically elongated rectangular projection 53", and the projection 53" is inserted into a rectangular guiding hole 34' provided through the center of the guide member 34 that is fixed on the front surface 31 of the movable body 30 to define the base surface. The grindstone mounting member 10 for carrying the grindstone 13 is screwed to the projection 53" and is attached to the stationary body 20, overlapping the base surface 34". It is noted that the longitudinal (vertical) length of the guiding hole 34' is longer than that of the projection 53", and the thickness (height) of the projection 53" is slightly larger than that of the guide member 34. The guiding hole 34' allows the projection 53" to displace only in the longitudinal direction.

In operation of the hand scaler sharpener unit discussed hitherto, first the grindstone 13 is mounted on the grindstone mounting member 10, the slant angle of the base surface 34" with respect to the level line is set, and then the motor is driven so as to move reciprocatingly the grindstone mounting member 10 with the grindstone 13 up and down on the base surface 34". The operation state of the sharpener unit will be discussed further in detail.

The slant angle of the grindstone 13 is set by adjusting the extent of projection of the movable body 30 through the opening of the stationary body 20 in the following manner. Namely, the operation knob 41 of the operation member 40 is manually pressed downward to thereby press down the rod member 25 that has been fit in one of the indexing grooves 33a–33f, into the groove 26 placed below against the thrusting force exerted on the rod member 25 by the springs 27. By this operation, the movable body 30 secured with respect to the stationary body 20 is released. Not being fixed, the movable body 30 thrust rotationally forward is manually adjusted to place desired one of the first to sixth indexing grooves 33a–33f just above the groove 26, and then the force applied from above onto the operation knob 41 is removed. This allows the rod member 25 to be lifted by the springs 27 into the selected one of the indexing grooves, to thereby re-secure the movable body 30 with respect to the stationary body 20 with the slant angles of the front surface 31, base surface 34", and thus the grindstone 13 corresponding to the selected one of the indexing grooves. It is noted that the first to sixth indexing grooves 33a–33f are designed so as to set, when the rod member 25 is fit therein, the grindstone 13 (base surface 34") at an angle of 90°, 80°, 70°, 60°, 50°, and 40°, respectively.

The grindstone 13, with its slant angle having been set, is driven as follows. The driving switch 56 is turned on to drive the motor 50. The rotation speed of the output axis of the motor 50 is reduced with the reduction gears 51, and then transmitted to the rotary member 52 to impart the eccentric shaft 52' a circular motion. The eccentric shaft 52' in the circular motion causes displacement of the direction converting member 53 via the horizontally extending slot 53', but the displacement of the member 53 is restricted to an up-and-down motion by the function of the projection 53" inserted into the guiding hole 34' through the guide member 34. The circular motion of the eccentric shaft 52 is thus converted to an up-and-down motion via the direction converting member 53 and the guide member 34, and then transmitted to the grindstone mounting member 10 and the grindstone 13. The range of the up-and-down displacement of the direction converting member 52 corresponds to the up-and-down displacement component (diameter) of the circular motion of the eccentric shaft 52'.

Figure 16:
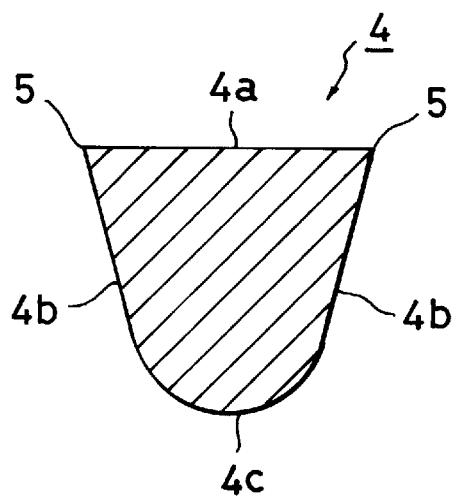
FIG. 16 is a cross-sectional view of the blade section.

By bringing the side 4b of the blade section 4 of a hand scaler 1 (FIG. 16) in parallel to and in contact with the surface of the grindstone 13 that is reciprocatingly moving up and down along the base surface 34" as discussed above, the cutting edge 5 of the blade section 4 may be restored easily to its original angle before wearing.

Figure 8:
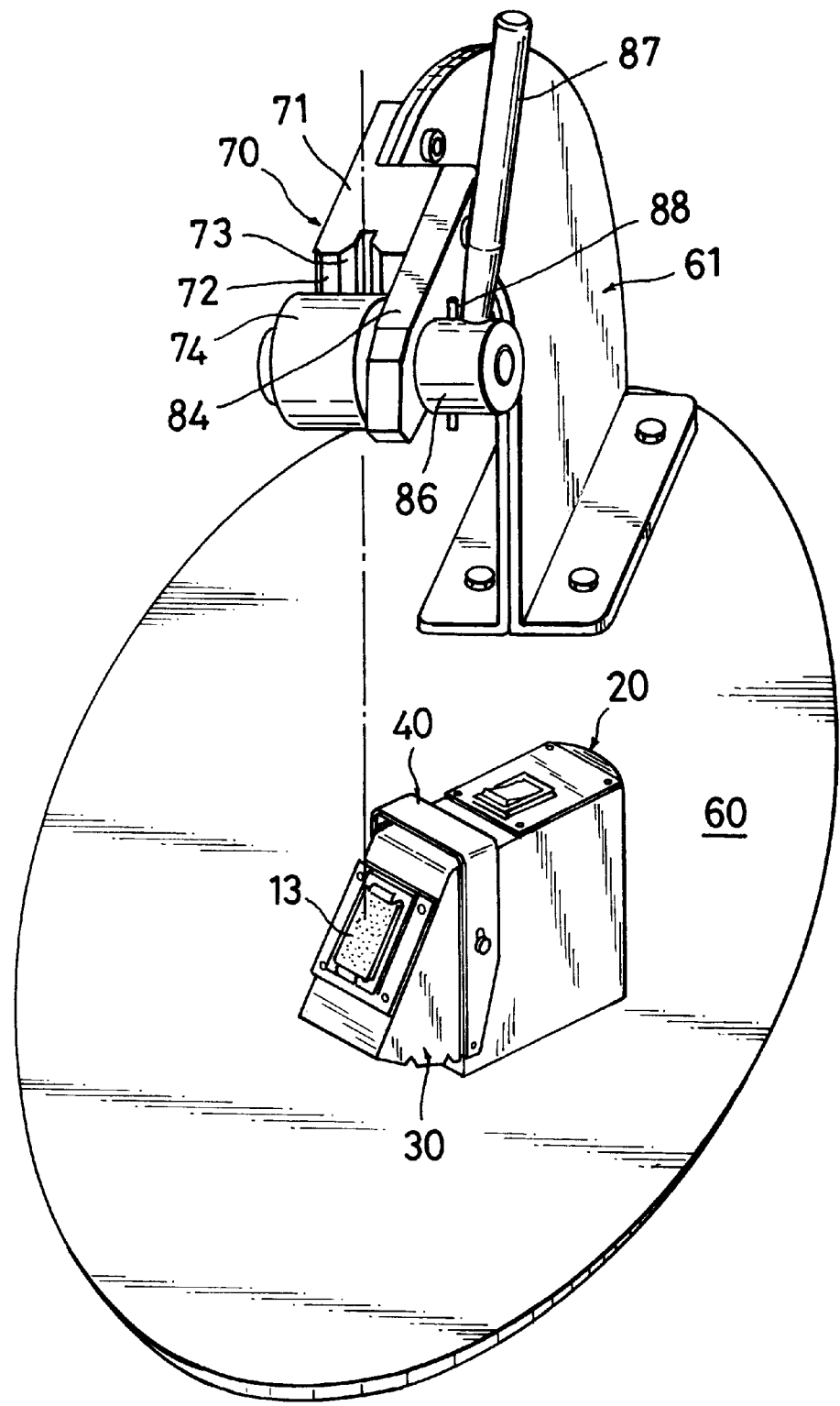
FIG. 8 is a perspective view of an embodiment of a hand scaler sharpening apparatus according to the present invention.

Next, discussion is made on the hand scaler sharpening apparatus of the present invention. The hand scaler sharpening apparatus is composed of, as shown in FIG. 8, the hand scaler sharpener unit as hitherto discussed in detail, and a hand scaler securing unit for securing a hand scaler 1 in generally a vertical direction during operation of the sharpener unit.

The hand scaler securing unit includes a base plate 60 for mounting and placing the sharpener unit in an appropriate position, a support arm 61 appropriately curved and erected on the base plate 60, and a securing unit body 70 attached to the upper end of the support arm 61.

Figure 9:
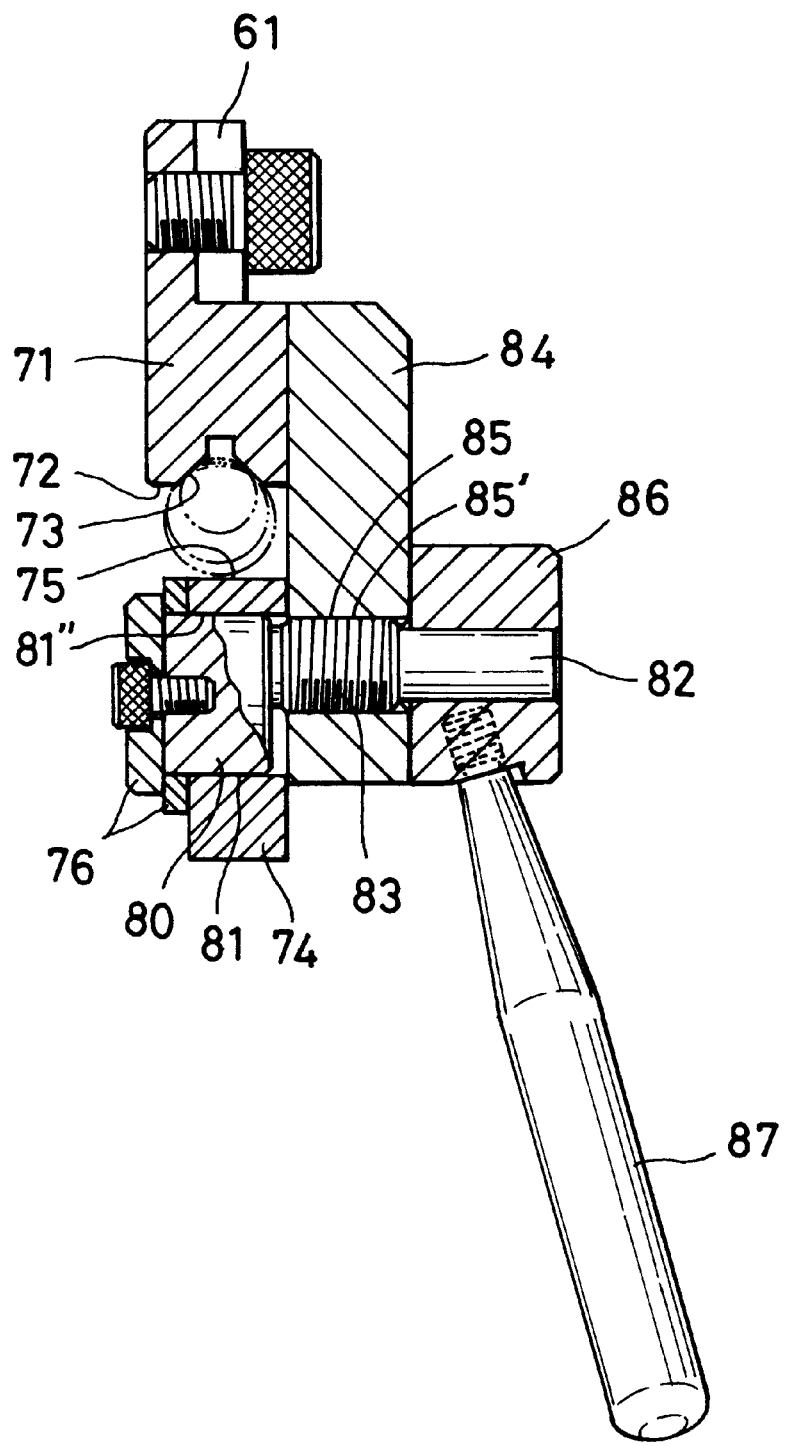
FIG. 9 is a horizontal cross-sectional view of a securing unit body.
Figure 10:
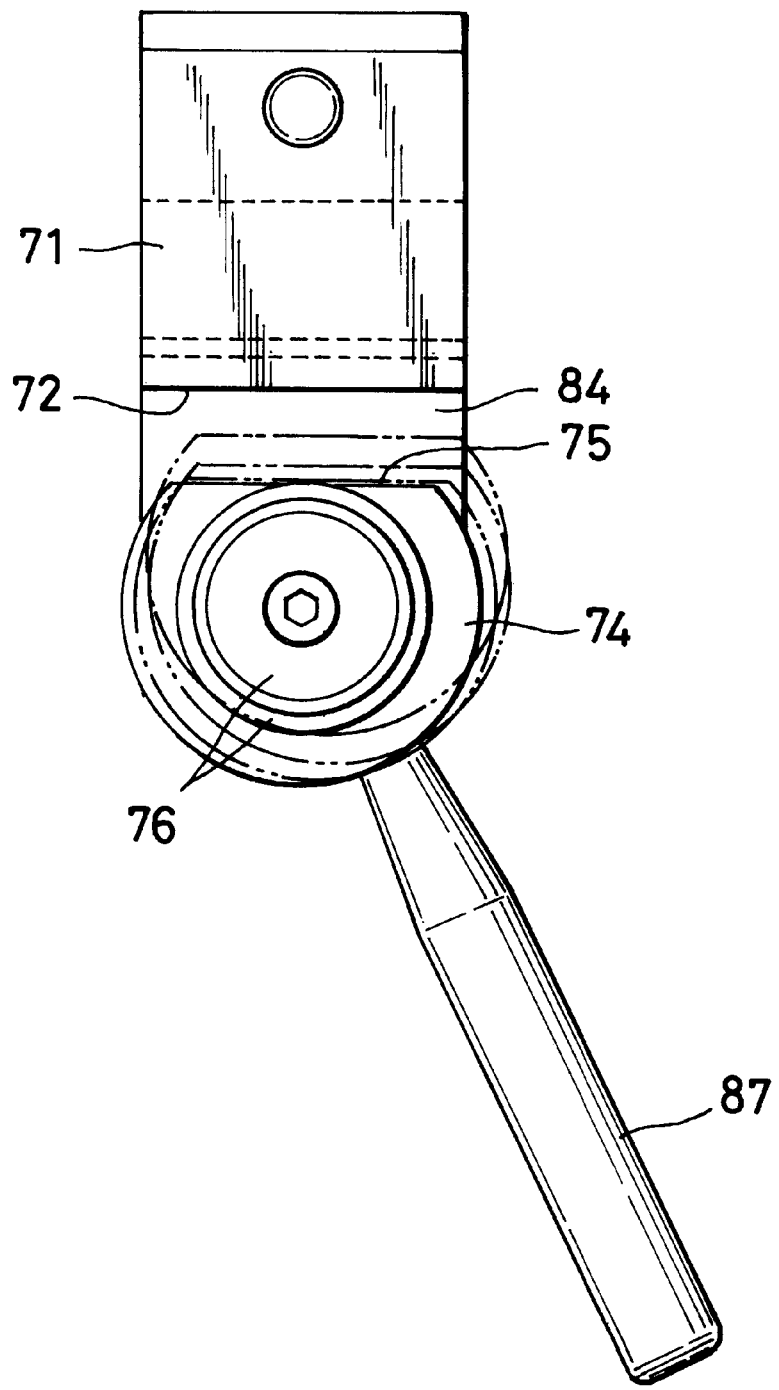
FIG. 10 is a left side view of the securing unit body.
Figure 11:
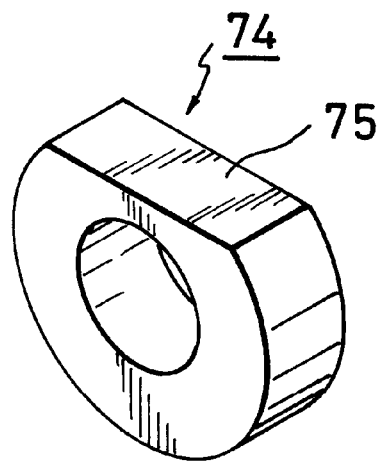
FIG. 11 is a perspective view of a cam roller.
Figure 12:
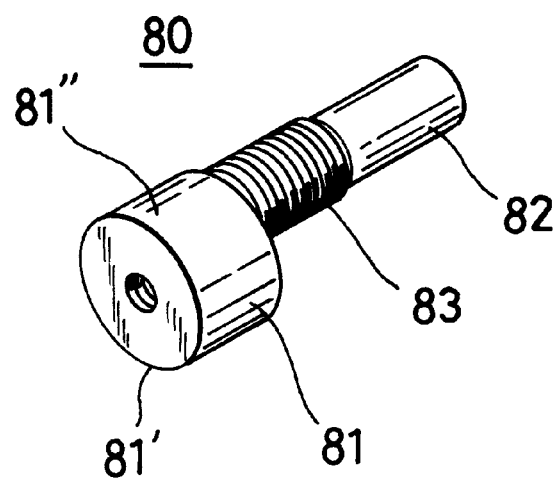
FIG. 12 is a perspective view of an eccentric cam.

The securing unit body 70 includes a stationary block 71 directly attached to the support arm 61, an annular cam roller 74 as a scaler clamping member for clamping the grip section 2 of a scaler 1 between the front face 72 of the stationary block 71 and the cam roller 74, and an eccentric cam 80 for displacing the cam roller 74 away from or closer to the front face 72 of the stationary block 71. The front face 72 of the stationary block 71 is provided with a grip seat 73 in the form of a generally vertically extending channel. The cam roller 74 has, as shown in FIG. 11, a cut-out surface 75 extending axially in parallel to the diameter of the cam roller. The eccentric cam 80 is composed of, as shown in FIG. 12, a cam body 81 in the form of a thick circular disk, and a cam shaft 82 extending eccentrically from the cam body 81. The cam roller 74 is rotatably (not integrally) fit around the outer periphery of the cam body 81, and is protected against dropping off the outer periphery of the cam body 81 by means of a roller retaining member 76 (FIGS. 9 and 10). The outer periphery of the cam body 81 has a longest radius portion 81' having the longest radius from the center of the cam shaft 82 (cam radius), and a shortest radius portion 81" having the shortest cam radius and located diametrally opposite to the longest radius portion 81'. The cam radius changes gradually between the longest radius portion 81' and the shortest radius portion 81".

The securing unit body further includes a cam shaft support member 84 supporting the cam shaft 82 of the eccentric cam 80, a cam shaft fixing member 86 in the form of a cylinder for fixing the right half of the cam shaft 82 therein, and an operation handle 87 obliquely projecting from the cam shaft fixing member 86. The cam shaft support member 84 is attached to the stationary block 71 at its proximal end, and has an axial bore 85 (FIG. 9) for passing the cam shaft 82 therethrough in its distal portion. The cam shaft 82 is passed through the axial bore 85 of the cam shaft support member 84, and received in the cam shaft fixing member 86, where the shaft 82 is unrotatably secured to the fixing member 86 by inserting a pin 88 (FIG. 8) into a bore (not shown) diametrally penetrating the cam shaft 82 and the cam shaft fixing member 86.

On the left half of the cam shaft 82 is provided an external thread portion 83, whereas on the axial bore 85 in the cam shaft support member 84 is provided an internal thread portion 85' for meshing with the external thread portion 83 on the cam shaft 82 to allow the external thread portion 83 to advance and regress. The external thread portion 83 on the cam shaft 82 is so called a left hand thread. Thus, the external thread portion 83 advances rightwards with counterclockwise (left handed) rotation in mesh with the internal thread portion 85', unlike an ordinary thread advancing with clockwise (right handed) rotation, and the tightening force between the external and internal thread portions gradually increases as it advances.

The operational state of the hand scaler securing unit is now discussed. In the initial state where a scaler 1 is not fixed in the securing unit body 70, the shortest radius portion 81" of the eccentric cam 80 faces to the grip seat 73 of the stationary block 71, as shown in FIG. 9, to give enough gap between the cut-out surface 75 of the cam roller 74 and the grip seat 73 for receiving a scaler 1. In this state, the operation handle 87 is oriented upward as shown in FIG. 8. Stating from this state, the scaler 1 may be secured in the securing unit body 70 simply by placing the grip section 2 of the scaler 1 to the grip seat 73 of the stationary block 71, and then turning the operation handle 87 backwards from the position shown in FIG. 8. That is, the operation of the operation handle 87 rotates counterclockwise the cam shaft fixing member 86 and thus the cam shaft 82 to cause the longest radius portion 81' of the cam body 81 to face to the grip seat 73 instead of the shortest radius portion 81". As a result, the cut-out surface 75 of the cam roller 74 gradually approaches to the scaler grip section 2 to clamp the grip section 2 between the grip seat 73 and the cut-out surface 75. This operation also results in rightward advancement of the external threat portion 83 in mesh with the internal thread portion 85' in the cam shaft support member 84 as the cam shaft 82 rotates counterclockwise, which increases the tightening force between the external and internal thread portions 83 and 85'. The increased tightening force between the external and internal thread portions 83 and 85' constrains the cam shaft 82 to secure the cam body 81, which in turn secures the cam roller 74, with the scaler grip section 2 being clamed between the grip seat 73 and the cam roller 74. Now the hand scaler 1 is held generally vertically with the securing unit mentioned above, with the inner surface 4*a* (FIG. 16) of the selected scaler blade section 4 being arranged horizontally. The cutting edge 5 may then be restored easily and uniformly using the sharpener unit wherein the angle of the surface of the grindstone 13 has been adjusted to be in parallel to the side 4*b* of the blade section 4.

For releasing the scaler 1, the operation handle 87 is to be turned simply in the opposite direction to return the handle 87 to the initial position.

Figure 13:
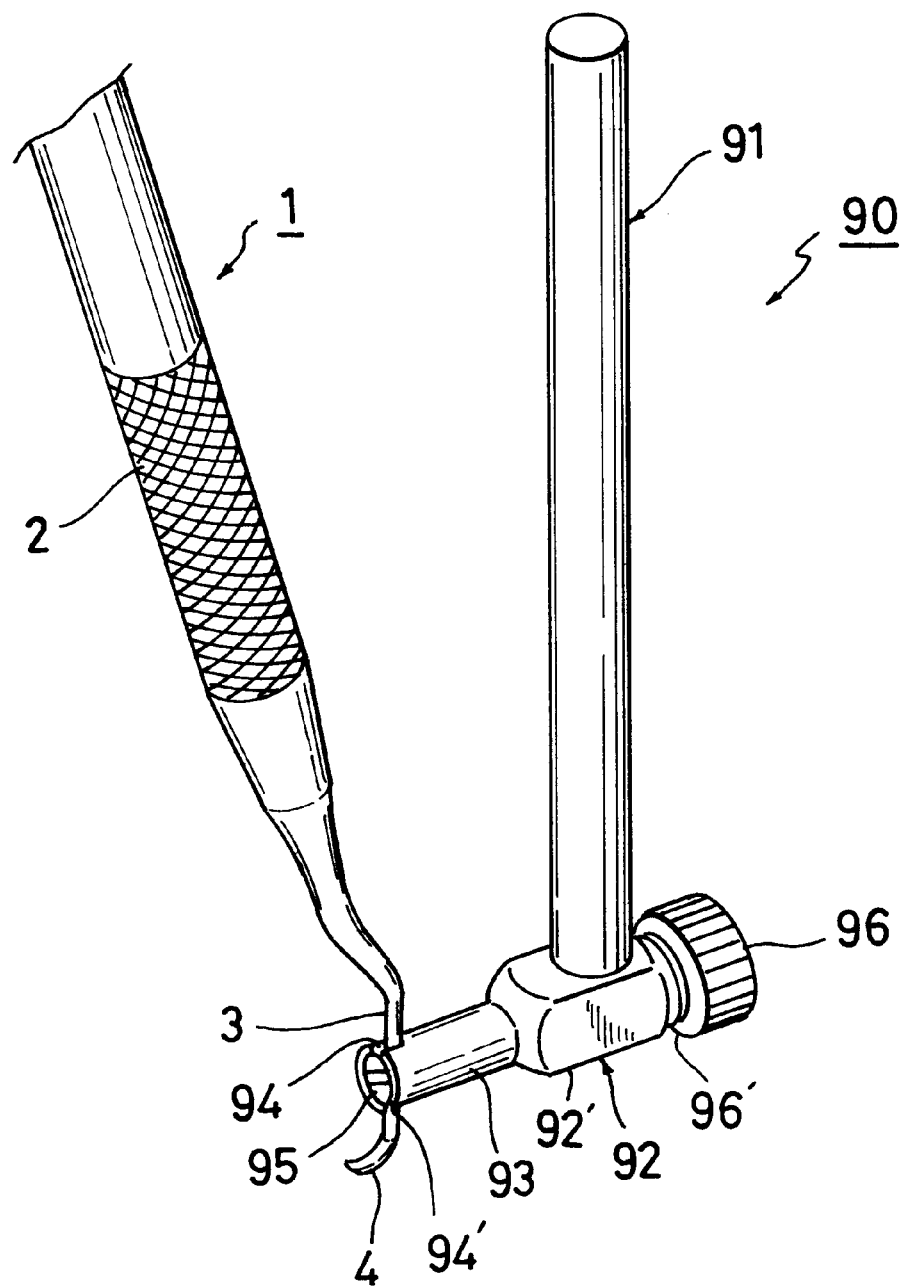
FIG. 13 is a perspective view of an indirectly securing member with a hand scaler.
Figure 14:
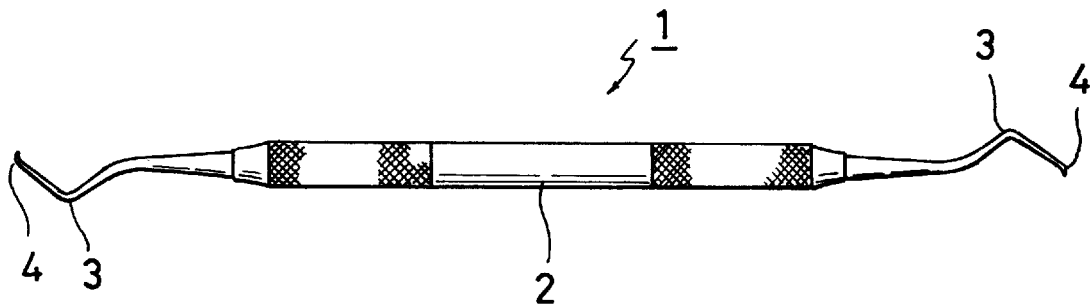
FIG. 14 is an overall view of a hand scaler.

The hand scaler sharpening apparatus according to the present invention may have, aside from the embodiment wherein the hand scaler 1 is directly secured to the securing unit body 70, another embodiment employing an indirectly securing member 90 shown in FIG. 13 wherein the scaler 1 is indirectly secured with respect to the securing unit body 70. The indirectly securing member 90 includes a rod portion 91 to be clamped, in place of the scaler grip section 2, between the grip seat 73 of the stationary block 71 and the cut-out surface 75 of the cam roller 74, and a scaler securing portion 92 connected to the lower end of the rod portion 91 with its longitudinal axis being perpendicular to the rod portion 91. The scaler securing portion 92 has a hollow prism portion 92' and a cylinder portion 93 projecting forward from the hollow prism portion 92' with slight reduction in the diameter. The hollow prism portion 92' and the cylinder portion 93 together define a space therein that extends through the two portions and opens at the front end of the cylinder portion 93 and at the rear end of the hollow prism portion 92'. The cylinder portion 93 is provided with notches 94, 94' at diametrally opposed top and bottom positions in its front end, respectively, for receiving the shank section 3 of the scaler 1. A shank securing member 95 is accommodated in the cylinder portion 93 for pressing the shank section 3 received in the notches 94, 94' rearwards to secure the shank section 3. The hollow prism portion 92' accommodates a screw 96' with its knob 96 being exposed outside at the rear end of the hollow prism portion 92', which knob 96 is formed integrally with the head of the screw 96'. Though not shown in the drawings, the shank securing member 95 is designed to displace backwards, when the knob 96 is turned in one direction, in the axial direction of the cylinder portion 93 due to the tightening of the screw 96', and to displace forwards, when the know 96 is turned in the opposite direction, in the axial direction due to the loosening of the screw 96'.

Thus, the scaler 1 may be secured to the scaler securing portion 92 by passing the scaler blade section 4 through the upper and lower notches 94 and 94' from above, with the shank securing member 95 in the forefront in the cylinder portion 93, to thereby place the scaler shank section 3 between the notches 94 and 94', and then turning the knob 96 in one direction. This causes backward displacement of the shank securing member 95, which presses the shank section 3 against the notches 94, 94' as shown in FIG. 13, thereby fixing the shank section 3 in place.

Figure 15:
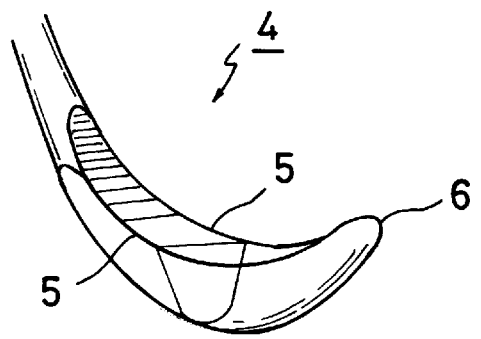
FIG. 15 is an enlarged perspective view of a hand scaler blade section in partial fragmentation.

With the indirectly securing member 90 as discussed above, the rod portion 91 is secured to the securing unit body 70 generally vertically, and the hand scaler 1 is fixed obliquely with respect to the rod portion 91. This positioning of the scaler 1 is suitable for sharpening the tip 6 (FIG. 15) of the blade section 4, for restoring a cutting edge 5 that has been deformed to an unusable extent, or for changing the angle of a cutting edge.

What is claimed is:

1. A hand scaler sharpener unit adapted to sharpen a hand scaler with a grindstone for restoration of the hand scaler, comprising:
    a base member having a base surface slanted at an angle to a level line;
    a grindstone mounting member for mounting a grindstone thereon; and
    a grindstone driving means for reciprocatingly moving said grindstone mounting member on and along said base surface.

2. The hand scaler sharpener unit of claim 1 wherein said base member comprises a stationary body and a movable body, said movable body rotatably connected to said stationary body and having said base surface defined thereon, said base member further comprising a slant angle setting means for fixing said movable body with respect to said stationary body to set a slant angle of said base surface.

3. The hand scaler sharpener unit of claim 2 wherein said movable body has a curved surface curved in a direction of rotation of the movable body with respect to the stationary body, and wherein said slant angle setting means comprises:
- a first elastic member for continuously thrusting said movable body in one direction of rotation,
- a plurality of recesses provided on said curved surface at intervals in the direction of rotation,
- an engagement member provided in the stationary body for engaging with a desired one of said recesses to secure the movable body with respect to the stationary body,
- a second elastic member for continuously thrusting said engagement member toward engagement with said one of the recesses, and
- an operation member for releasing said engagement of the engagement member with said one of the recesses against thrust of the second elastic member.

4. The hand scaler sharpener unit of claim 3 wherein said plurality of recesses are provided on the curved surface at 10° intervals in the direction of rotation.

5. The hand scaler sharpener unit of claim 1 wherein said grindstone driving means comprises:
- a motor,
- an eccentric shaft driven by said motor to make a circular motion, and
- a driving direction converting means for converting said circular motion of the eccentric shaft to a reciprocating motion of the grindstone mounting member along the base surface.

6. A hand scaler sharpening apparatus comprising the hand scaler sharpener unit of claim 1, and a hand scaler securing unit for securing a hand scaler generally vertically during operation of the sharpener unit.

7. The hand scaler sharpening apparatus of claim 6 wherein said hand scaler securing unit comprises a securing unit body and a support member for supporting said securing unit body at a desired height, said securing unit body comprising:
- a stationary member fixed to the support member,
- a scaler clamping member for clamping a grip section of a hand scaler between said stationary member and said scaler clamping member,
- a distance adjusting means for adjusting a distance of said scaler clamping member from the stationary member, and
- a securing means capable of securing the scaler clamping member with said grip section being clamped between the stationary member and the scaler clamping member,
- wherein said securing means is designed to be capable of securing the scaler clamping member by constraining the distance adjusting means, and to gradually increase constraining force exerted on the distance adjusting means by the securing means as the scaler clamping means moves closer to the stationary member.

* * * * *